(12) United States Patent
Trainoff

(10) Patent No.: US 9,335,250 B2
(45) Date of Patent: May 10, 2016

(54) BUBBLE SUPPRESSING SYSTEM FOR OPTICAL MEASUREMENT CELLS

(75) Inventor: Steven P. Trainoff, Goleta, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 20 days.

(21) Appl. No.: 14/236,886

(22) PCT Filed: Aug. 3, 2012

(86) PCT No.: PCT/US2012/049641
§ 371 (c)(1),
(2), (4) Date: Feb. 3, 2014

(87) PCT Pub. No.: WO2013/022795
PCT Pub. Date: Feb. 14, 2013

(65) Prior Publication Data
US 2014/0160463 A1    Jun. 12, 2014

Related U.S. Application Data

(60) Provisional application No. 61/515,796, filed on Aug. 5, 2011.

(51) Int. Cl.
*G01N 21/15* (2006.01)
*G01N 21/01* (2006.01)
(Continued)

(52) U.S. Cl.
CPC ............... *G01N 21/01* (2013.01); *G01N 21/05* (2013.01); *G01N 21/11* (2013.01); *G01N 21/53* (2013.01);
(Continued)

(58) Field of Classification Search
CPC .............. G01N 2001/2267; G01N 2015/0011; G01N 2015/1068; G01N 2021/054; G01N 2035/1018; G01N 2001/1445; G01N 2001/1454; G01N 2001/1463; G01N 21/01; G01N 21/05; G01N 21/11; G01N 21/53; G01N 21/85; G01N 27/44721; G01N 27/44704; G01N 21/15
USPC ........................................................ 356/246
See application file for complete search history.

(56) References Cited

U.S. PATENT DOCUMENTS 4,076,420 A * 2/1978 De Maeyer et al. ............ 356/73
4,222,670 A * 9/1980 Koshiishi ....................... 356/414
(Continued)

FOREIGN PATENT DOCUMENTS

EP  0 924 506 A1  6/1999
JP  H04-194652 A  7/1992
(Continued)

OTHER PUBLICATIONS

Zhang, Yongzhong, Instrument Analysis, China Agriculture Press, 2008, pp. 271-276, China.
(Continued)

*Primary Examiner* — Michael P Lapage
(74) *Attorney, Agent, or Firm* — David N. Villalpando; Philip J. Wyatt

(57) ABSTRACT

A method and apparatus is disclosed for suppression of bubbles in an optical measurement cell. A measurement cell is filled with a fluid sample. Valves connected through plumbing connections to the cell are operated such that any flow in and out of the cell is stopped. A pressure source is then applied through a valve and flow impedance mechanism to the liquid contained within the cell, causing any bubbles contained or generated within the cell to be dissolved back into solution or reduced in size such that optical measurements taken of the sample are more accurate and free of interference with the measurement beam and of measured stray light. Possible pressure sources include compressed gas, a piston, and a constant flow-rate pump.

25 Claims, 5 Drawing Sheets

(51) Int. Cl.
  *G01N 21/05*   (2006.01)
  *G01N 21/11*   (2006.01)
  *G01N 21/53*   (2006.01)
  *G01N 21/85*   (2006.01)
  *G01N 21/03*   (2006.01)
  *G01N 27/447*   (2006.01)

(52) U.S. Cl.
  CPC .......... *G01N 21/85* (2013.01); *G01N 27/44721* (2013.01); *G01N 21/15* (2013.01); *G01N 27/44704* (2013.01); *G01N 2021/0346* (2013.01); *G01N 2021/054* (2013.01)

(56) References Cited

U.S. PATENT DOCUMENTS

| | | | |
|---|---|---|---|
| 5,358,613 A * | 10/1994 | Schneider et al. | 204/453 |
| 6,004,443 A | 12/1999 | Rhodes et al. | |
| 6,172,376 B1 * | 1/2001 | Xu et al. | 250/574 |
| 6,297,505 B1 * | 10/2001 | Frandsen | G01N 21/05 250/339.12 |
| 2003/0177812 A1 * | 9/2003 | Joseph et al. | 73/1.71 |
| 2005/0269264 A1 * | 12/2005 | Fermier et al. | 210/635 |
| 2006/0114467 A1 | 6/2006 | Nicoli et al. | |
| 2006/0129084 A1 * | 6/2006 | Miyato | 604/19 |
| 2007/0187633 A1 * | 8/2007 | Fisher et al. | 250/576 |
| 2007/0257215 A1 * | 11/2007 | Rich | 250/574 |
| 2008/0116073 A1 | 5/2008 | Soji et al. | |
| 2008/0221814 A1 * | 9/2008 | Trainer | 702/70 |
| 2008/0302959 A1 * | 12/2008 | Amirav | 250/283 |
| 2010/0150781 A1 | 6/2010 | Ervin et al. | |
| 2010/0231909 A1 | 9/2010 | Trainer | |
| 2011/0140706 A1 | 6/2011 | Groves | |

FOREIGN PATENT DOCUMENTS

| | | | |
|---|---|---|---|
| JP | H04194652 | * 7/1992 | ............. G01N 21/59 |
| JP | H07-72049 A | 3/1995 | |
| JP | 2002/005946 A | 1/2002 | |
| JP | 2002-174458 A | 6/2002 | |
| JP | 2005-221397 A | 8/2005 | |
| WO | 98/20338 A1 | 5/1998 | |
| WO | 2005/091936 A2 | 10/2005 | |

OTHER PUBLICATIONS

Zhong, Peihang, et.al., Using Backpressure Column to Replace Solvent Degassing in HPLC Analysis, Analysis and Testing Bulletin, 1985, pp. 42 and pp. 52, vol. 4, Issue 4 China.

* cited by examiner

BUBBLE SUPPRESSING SYSTEM FOR OPTICAL MEASUREMENT CELLS

PRIORITY

This application claims priority to U.S. Provisional Application No. 61/515,796, filed Aug. 5, 2012, "Method and apparatus to suppress bubbles in optical measurement cells."

RELATED APPLICATIONS AND PATENTS

The following patents relate to measurement of the electrophoretic mobility of particles and are hereby incorporated by reference:

U.S. Pat. No. 8,441,638 B2, H.-T. Hsieh and S. Trainoff, "Apparatus to measure particle mobility in solution with scattered and unscattered light," issued May 14, 2013.

U.S. Pat. No. 8,525,991 B2, H.-T. Hsieh and S. Trainoff, "Method to measure particle mobility in solution with scattered and unscattered light," Issued Sep. 3, 2013.

BACKGROUND

The invention discloses an innovative method and apparatus by which bubbles may be suppressed in optical measurement cells, including, but not limited to electrophoretic mobility measurement cells, wherein the motion of charged particles in a solution subject to an applied electric field is measured. Although the present invention will refer to macromolecules throughout much of its specification, measurement cells capable of bubble suppression using the inventive method and apparatus disclosed herein may include more generally all classes of small particles including emulsions, viruses, nanoparticles, liposomes, macro-ions and any other solution constituents whose size may lie between about a half and a few thousand nanometers. Thus whenever the terms "molecule," "macromolecule," or "macro-ion" are used, it should be understood to include all of the aforementioned solution-borne objects to be subject to some form of optical measurement.

Electrophoretic mobility is the directly measurable and most widely used quantity to characterize the charge of molecules, or other particles in solution. Once measured, the electrophoretic mobility can be used in turn to determine the effective charge, Ze, carried by such molecules as well as their so-called zeta potential $\zeta$. The interface between the group of ions tightly bound to the particle and those of the surrounding solution that do not move with the particle defines the hydrodynamic shear plane. The zeta potential represents the electrostatic potential existing at this shear plane. It is an objective of the present invention to improve optical measurements of electrophoretic mobility, effective charge, and zeta potential of molecules and particles in solution contained within an optical measurement cell. It should be noted, however, that the present inventive method and apparatus is not limited to measurements based on particle charge. Other measurements, such as multi-angle light scattering, MALS, and quasi-elastic light scattering, QELS, also often referred to as dynamic light scattering, DLS, wherein a light source is passed through an optically transparent measurement cell to illuminate a liquid sample contained therein, are among the other techniques which will benefit from the inventive elements disclosed herein. Therefore, while this disclosure will focus mainly on the utility of the invention as applied to mobility measurement cells, it should in no way be considered limited to this measurement technique or application.

Several techniques have been developed and are available for measuring mobilities including light scattering methods such as heterodyne DLS including both laser Doppler electrophoresis, LDE, and phase analysis light scattering, PALS. These techniques involve measuring light scattered from moving particles, whereby such scattered light carries information relating to such motion and from which the associated electrophoretic mobility of the particles may be determined.

The most significant of these techniques for the measurement of electrophoretic mobilities is PALS, where a beam of monochromatic light, usually from a laser source, illuminates a sample of liquid borne particles exposed to an applied electric field. Some of the light they scatter is collected and combined with a fraction of the incident, unscattered light. In other words, the scattered signal is combined coherently with the incident light to produce a heterodyned signal producing interference fringes at a detector. In order to measure the fluctuations of the combined beams and derive therefrom measurement of the electrophoretic mobility of the scattering particles, the incident beam fraction is directed to reflect from an oscillating mirror. This causes the detected fringes to exhibit an intensity modulation, even in the absence of electrophoretic motion. The electrophoretic motion that results from the application the applied field produces an additive frequency shift permitting, thereby, an unequivocal determination of the direction of the particles relative to the direction of the applied electric field. This process requires very precise measurement of light scattered from the sample. Bubbles contained within the illuminated sample scatter light that interferes with that scattered from the molecules, corrupting the derived measurements.

When making light scattering measurements, maintaining a bubble free environment is always a challenge. There are many ways of attempting to introduce a bubble free sample to a measurement cell including, but not limited to: vibrating, tapping, rinsing with alcohol, or even intentionally flushing the cell with air. While these may be helpful, it often happens that bubbles adhere to the surfaces. Even if a bubble-free sample is achieved, the electrical current that gives rise to the electrophoretic molecular motion can also cause electrolysis of the solvent resulting in bubbles that form on the electrodes. The problem becomes worse as the ionic strength of the buffer is increased because a progressively larger current is required to achieve a given electric field. Large currents generate more bubbles. Another objective of the present invention is to reduce the number and size of such bubbles that can interfere with electrophoretic measurements.

Additionally, samples that contain gas in solution or that undergo a chemical reaction, may spontaneously generate bubbles even in the absence of an applied field. Another objective of the present invention is to suppress such spontaneous bubble formation.

A BRIEF DESCRIPTION OF THE INVENTION

An innovative apparatus and method is disclosed producing automatic pressurization of an optical measurement cell containing a liquid sample introduced therein and reducing, thereby, the presence of bubbles. A series of valves are used to introduce the sample into the subsequently flushed and pressurized cell. A wide variety of pressure sources may be employed.

A BRIEF DESCRIPTION OF THE DRAWINGS

A DETAILED DESCRIPTION OF THE INVENTION

Figure 1:
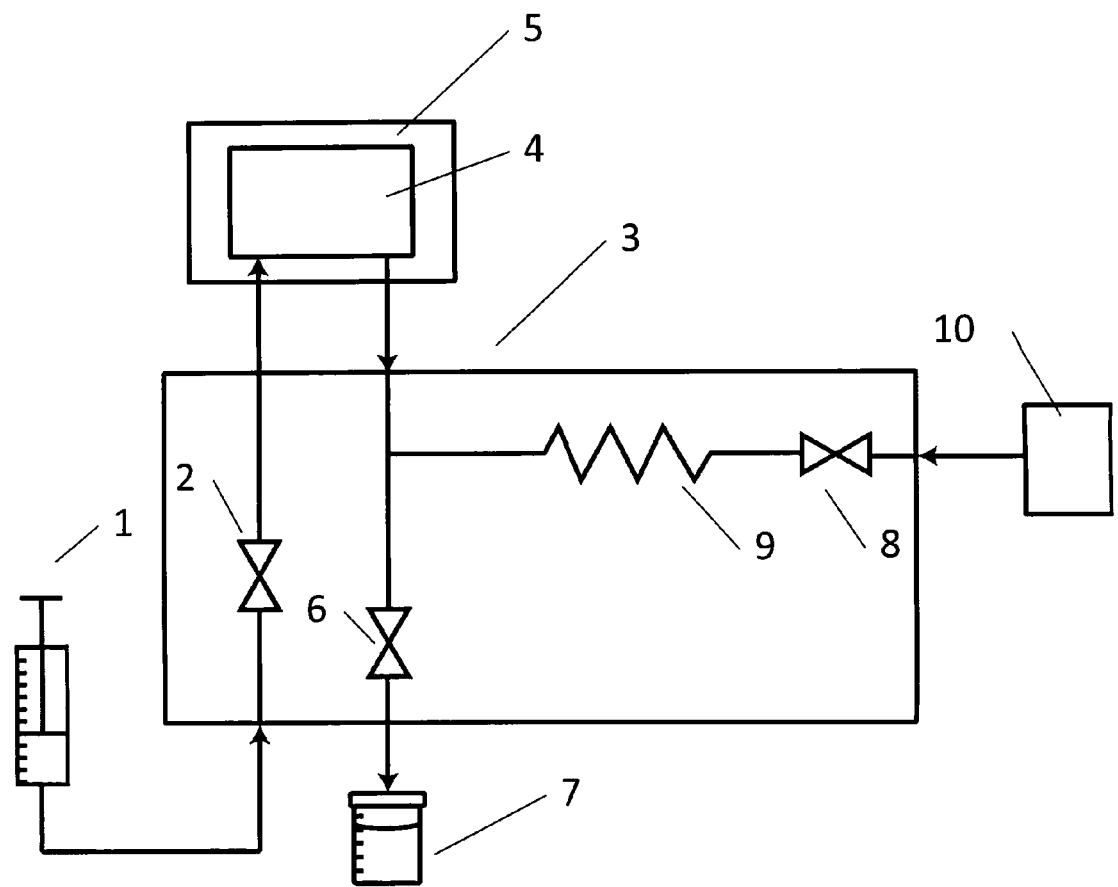
FIG. 1 shows a basic pressurization system, including three valves, for suppressing bubbles in an optical measurement cell.

All optical measurements of liquid borne samples are subject to uncertainties arising from bubbles being contained or generated in such samples. Multi-angle light scattering and quasi-elastic light scattering measurements can, for example, be prone to tiny bubbles accidentally injected into the measurement cell. These bubbles can cause errors in the measured values, or even make measurement impossible. In addition, some samples may be saturated with gasses to the point that, while they are present in the cell, bubbles form therein, again making measurements of the scattered light inaccurate or impossible. Electrophoretic mobility measurements are even more susceptible to inaccuracies in derived measurements due to bubbles contained within the cell. In addition to the possibility of injected and precipitated bubbles, the mechanism by which electrophoretic mobility is often measured includes the passing of a current through the liquid sample by means of electrodes contained within the cell. This procedure may cause electrolysis of the sample solvent and the creation of bubbles on the electrodes, which may then be released into the sample and frequently intersect the incident light beam, scattering light which can be misinterpreted as originating from the solvated sample or otherwise affecting the scattered light signals. When high ionic strength buffers are used, the bubble problem is exacerbated, as a correspondingly higher current must be passed through the sample to achieve the required electric field. The current electrolyzes the solvent, generating gas that may be released in the form of bubbles.

Pressurizing a sample cell can help reduce bubbles by three distinct mechanisms. The first is that, according to Boyle's law, the volume of a gas bubble is inversely related to the ambient pressure. For example, if a residual bubble is present after the cell is filled, pressurizing the cell to 10 bar will reduce the bubble volume by a factor of 10. Even though the bubble is still present, its potential for contributing to stray light will be reduced significantly.

A second means by which pressurizing helps reduce bubble formation is by changing the solubility of gas in liquid. According to Charles' law, the solubility of gas is directly proportional to ambient pressure. For example, if one pressurizes the cell to 10 bar, the amount of gas that can dissolve into solution also increases by a factor of 10. The increased solubility causes the gas in the bubbles to go into solution, thereby reducing their volumes beyond that dictated by Boyle's law or eliminating them altogether. The higher the solubility, the more rapidly this process occurs because the difference in the ambient pressure and solubility tension is increased by the same factor of 10.

A third means to reduce bubble presence is through the modification of the Laplace pressure inside the bubble. As stated earlier, bubble volume decreases inversely proportional to the pressure. However, smaller bubbles also have increased surface tension due to their higher radius of curvature. This causes the pressure inside the bubble to be higher than the ambient pressure. The net effect of this overpressure is to increase the rate with which gas is driven from the bubble into solution. Small bubbles dissolve faster than larger ones.

Bubbles otherwise arising from injection, precipitation, electrolysis, or other means may be mitigated by the inventive method and apparatus disclosed herein. The apparatus allows automatic pressurization of an optical measurement cell such as used for light scattering or mobility measurements. While it is possible to make QELS or MALS measurements while the sample is flowing, static, or in stop flow mode, it is important to note that electrophoretic mobility measurements can only be made in stop flow mode. The common method of pressurizing a flow cell by putting a small capillary on the exit and making the measurement while the sample is pumped through cannot be used because the motion of the sample due to the applied flow would completely dwarf the motion induced by the applied electric field.

In the particular case of an electrophoretic mobility measurement, the applied electric field may generate electrolysis products, typically hydrogen and oxygen. These products can go either into solution or can be released as bubbles. Higher ambient pressures force the gasses to preferentially go into solution instead of being released as bubbles.

There are three phases of operation: load, pressurization, and release. In the load phase, a sample is introduced by means of an injector 1 through an open inlet valve 2 into the pressurization system 3 and then into the optical measurement cell 4 contained within a measurement instrument 5. The outlet valve 6, also in the open position allows overflow fluid to exit the cell and pressurization system and go to waste 7. During this loading phase, pressure valve 8 is in the closed position, which blocks most sample from entering the trapped arm containing a flow impedance 9 that sets the rate at which the cell pressurizes. A large impedance allows the system to pressurize slowly preventing undue mechanical stress. The injector 1 may take any number of forms including a manually operated syringe, a syringe pump, an auto-injector, or any other injection system. In addition, the flow impedance mechanism 9 may also take many forms, including narrow capillary tubing, a guard column, a membrane, a filter, etc.

In the pressurization phase, closing the inlet valve 2 and outlet valve 6, and opening the pressure valve 8 pressurizes the system. The sample in the cell is then static. It equilibrates to the same pressure as the pressure source 10.

In the release phase, after the measurement is taken or pressurization in the cell is no longer desired, the pressure valve 8 is closed, and the outlet valve 6 is opened causing any sample trapped in the impedance mechanism 9 to be flushed to waste 7 as the system depressurizes. Finally the inlet valve 2 is opened and a new sample may be injected.

A wide variety of pressure sources 10 and media may be used, either liquid or gaseous. It is important to note that the system applies the pressure through the impedance mechanism 9, which is located on the exit side of the cell. During the pressurization phase inlet valve 2 is closed so there is no flow of the pressurization media into the cell 4. In the release phase, the pressurization media exits to waste 7. At no point is the sample in the measurement cell in contact with the pressurization media.

Figure 2:
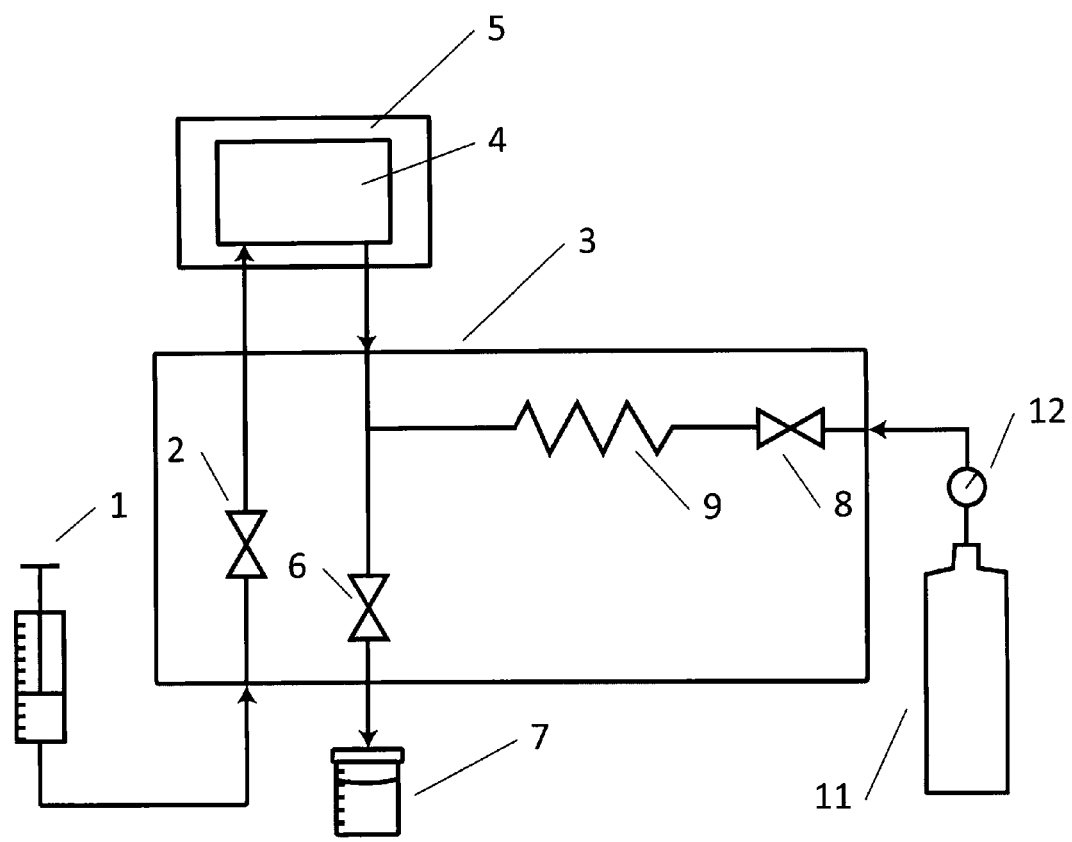
FIG. 2 illustrates the pressurization system employing a gas contained within a pressurized cylinder as the pressurizing medium.

As shown in FIG. 2, the simplest embodiment of the system uses a cylinder of compressed gas 11 along with a pressure regulator 12 to set the system pressure. Adjusting the regulator sets the value of the system pressure. Although a gas cylinder is convenient, it needs to be periodically refilled. An alternative embodiment would employ a small on-demand compressor to periodically refill the gas cylinder.

Figure 3:
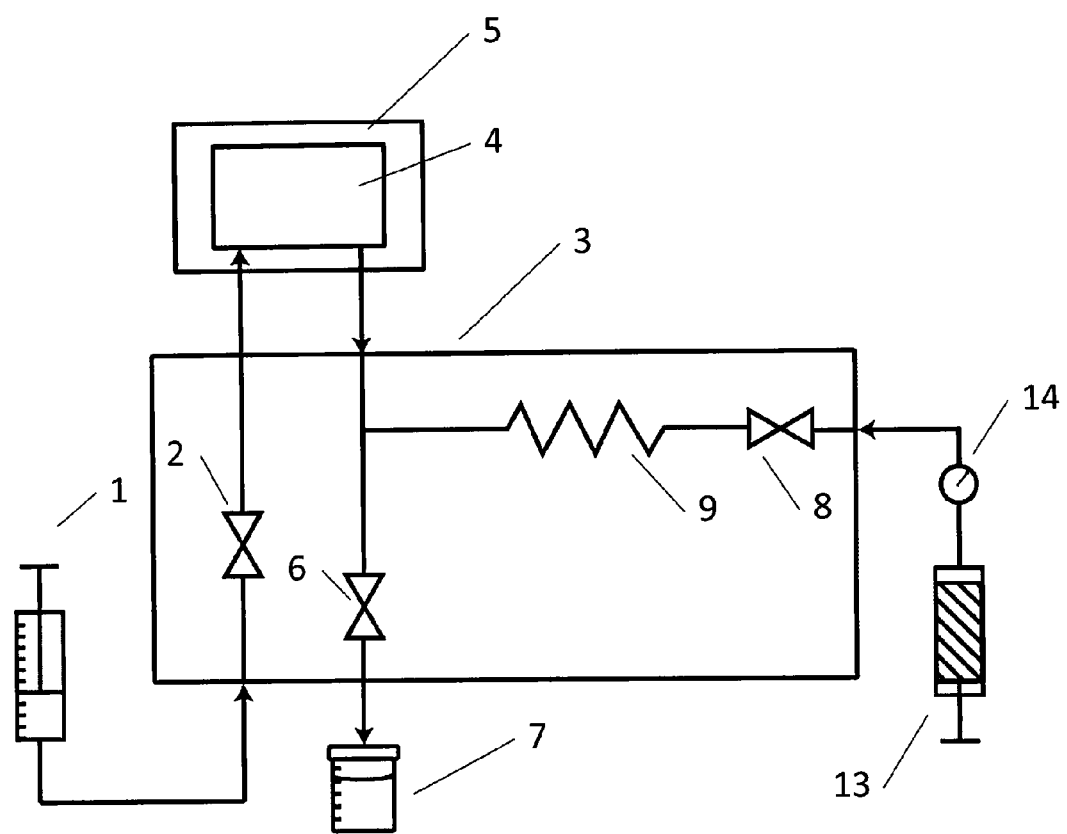
FIG. 3 represents the pressurization system employing a piston as a pressure source.

Another embodiment of the inventive apparatus employs the application of a known force to a piston 13 to act as the pressure source 8 as shown in FIG. 3. The force applied to the piston could be a static force, such as a weight, but clearly an electrically actuated piston would have the same effect. Adjusting the force applied at the piston sets the pressure. In theory, the pressure applied to the fluid is simply the force divided by the cross sectional area of the piston, although in practice, friction on the piston causes the applied pressure to be somewhat smaller than this. Therefore, in order to know the precise value of the applied pressure, a gauge 14 may be included to measure the actual pressure applied. This embodiment, however, may be less desirable than others, as the fluid contained in the piston is essentially trapped, while the embodiment, for example, using compressed gas flushes the pressurization medium out of the waste line after each depressurization.

Figure 4:
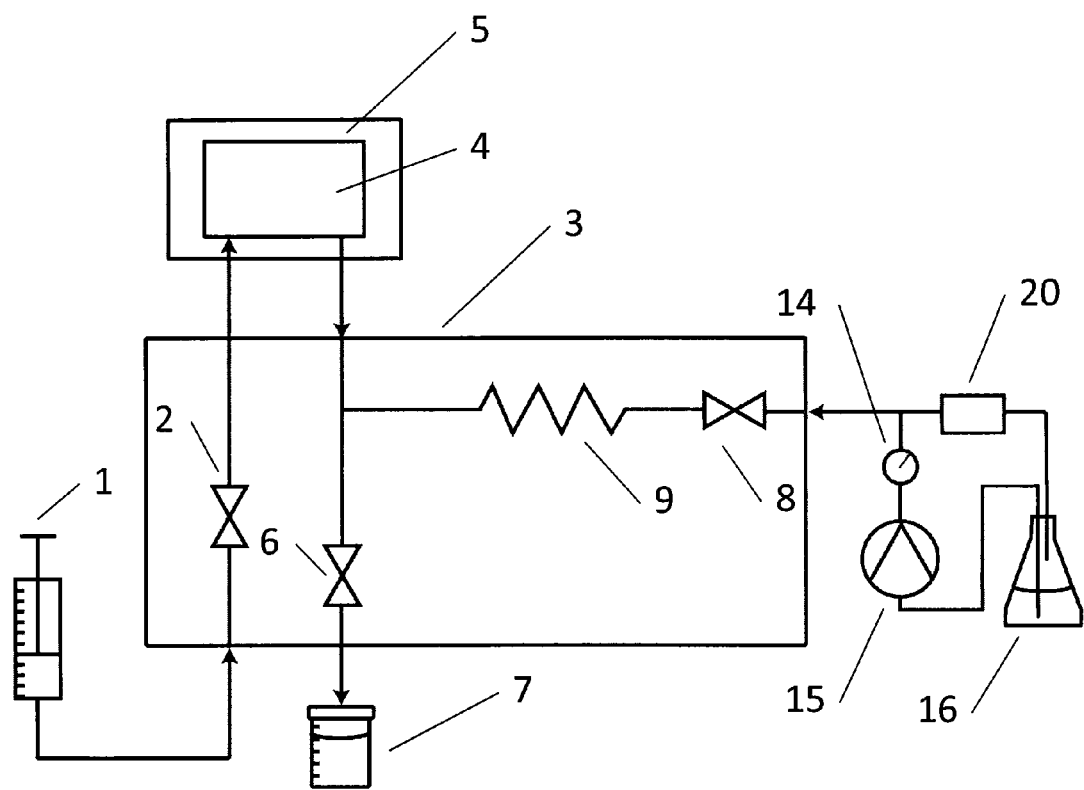
FIG. 4 illustrates the pressurization system employing a pump as a pressure source.

Another embodiment, as shown in FIG. 4, uses a constant velocity pump 15 that recirculates fluid from a reservoir 16 through an impedance or back pressure regulator 20 back into the reservoir. When element 20 is a flow impedance, adjusting the flow rate sets the system pressure. When element 20 is a back pressure regulator, the flow rate is irrelevant as long as it is high enough that the pump is stable. Like the gas cylinder embodiment presented above, there is no trapped fluid as the pressurization medium is flushed out of the system after each depressurization cycle.

Figure 5:
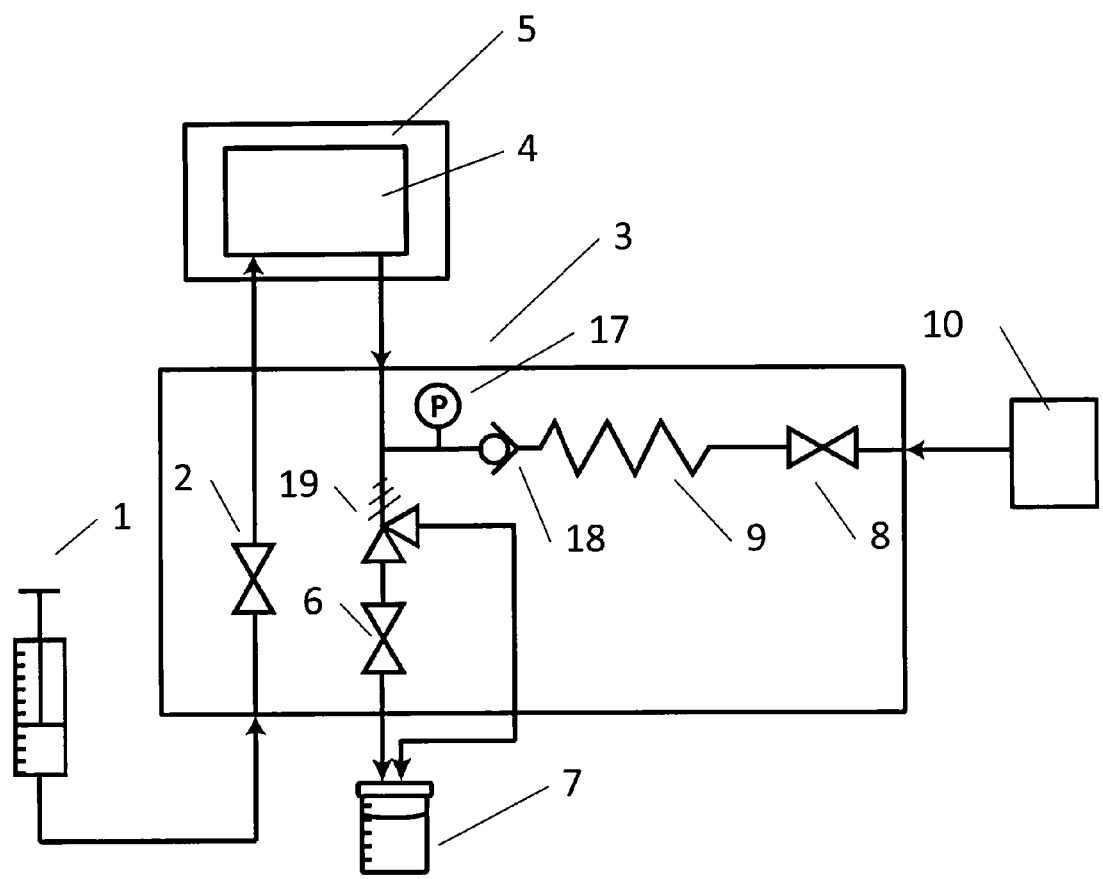
FIG. 5 illustrates another embodiment of the pressurization system of FIG. 1 with optional elements including a pressure relief valve connected to waste, a check valve to prevent back flow, and a pressure sensor.

The embodiment of the invention shown in FIG. 5 includes additional elements, which aid in the prevention of damage to the measurement cell in the case of over pressurization, or accidentally attempting to introduce a new sample while the system is pressurized. A pressure sensor element 17 permits the monitoring of the pressure applied to the measurement cell. Check valve 18 prevents back flow from the injection system into the pressure source and may be located anywhere along the pressurization arm of the system. A pressure relief valve 19 is connected by tubing to waste 7 preventing over pressurization which could otherwise result in leakage, damage to the system 3, or damage to the measurement cell 4 itself.

The inventive apparatus may also be used to check the integrity of the measurement instrument 5 for leaks. One pressurizes the cell by the mechanism described above, and then one closes valve 8 to isolate the pressure source from the rest of the system, which now forms a sealed volume. One then monitors the pressure of gauge 17 over time. If there is a leak the pressure will decay over time. If the measured drop exceeds a predetermined rate, the system has detected a leak, and an alarm can be raised. The pressurization system 3 can check itself for leaks if instrument 5 is replaced with a length of tubing that loops the pressurization system back to itself. In an embodiment wherein the valves are electrically actuated, waste heat from the valves can cause pressure changes even in the absence of a leak, therefore temperature regulation of the valve bodies increases the sensitivity of the system, allowing it to detect smaller leaks.

As will be evident to those skilled in the arts of optical measurements and fluid dynamics that there are many obvious variations of the methods and devices of the invention that do not depart from the fundamental elements that disclosed herein; all such variations are but obvious implementations of the described invention and are included by reference to our claims, which follow.

The invention claimed is:

1. A system to suppress bubbles within a liquid sample, contained in an optical measurement cell, comprising
   A. a measurement arm with elements connected in series by tubing there between, wherein fluid passes sequentially through said measurement arm elements, said measurement arm elements comprising
      a. an inlet sample injection port;
      b. an inlet valve;
      c. an optical measurement cell comprising an inlet to optical measurement cell port and an outlet from optical measurement cell port;
   B. a waste arm with elements connected in series by tubing there between, wherein fluid passes sequentially through said waste arm elements, said waste arm elements comprising,
      a. an inlet from optical measurement cell port;
      b. an outlet valve;
      c. an outlet to waste port;
   C. a pressurization arm with elements connected in series, wherein fluid passes sequentially through said pressurization arm elements, said pressurization arm elements comprising;
      a. a pressurization source;
      b. a pressure valve;
      c. a flow impedance means comprising a length of flow restricting capillary tubing, said flow impedance means enabling the system to pressurize slowly minimizing, thereby, mechanical stress to said optical measurement cell during pressurization; and
      d. an outlet to system port; and
   D. a tee union comprising at least three ports wherein said tee union ports are independently connected by tubing to
      a. said outlet from optical measurement cell port of said measurement arm;
      b. said inlet from optical measurement cell port of said waste arm; and
      c. said outlet to system port of said pressurization arm.

2. The system of claim 1 where said optical measurement cell is an element of an electrophoretic mobility detector, said optical measurement cell comprising electrodes by means of which an electric field is induced within said liquid sample contained within said optical measurement cell.

3. The system of claim 2 where said electrophoretic mobility detector is a phase analysis light scattering detector.

4. The system of claim 1 where said optical measurement cell is an element of a light scattering photometer.

5. The system of claim 1 where said inlet valve is a check valve.

6. The system of claim 1 where said inlet valve is an electrically actuated valve.

7. The system of claim 1 where said inlet valve, said outlet valve and said pressure valve are electrically actuated valves.

8. The system of claim 1 further comprising a check valve connected between said flow impedance means and said outlet valve.

9. The system of claim 1 further comprising a pressure relief valve connected between said tee union and said outlet valve.

10. The system of claim 1 further comprising a pressure sensor connected between said pressurization means and said optical measurement cell, such that said pressure sensor enables measurement of the pressure applied to said optical measurement cell by said pressurization source.

11. The system of claim 1 where said pressurization source is a cylinder of compressed gas connected to a pressure regulator which determines the applied pressure.

12. The system of claim 11 further comprising an on-demand compressor.

13. The system of claim 1 where said pressurization source is a piston.

14. The system of claim 1 further comprising a pressure gauge that monitors the pressure applied by said pressurization source.

15. The system of claim 1 where said pressurization source is a liquid pump recirculating through a second flow impedance means.

16. The system of claim 15 where said liquid pump is a constant velocity pump.

17. The system of claim 1 where said pressurization source is a liquid pump recirculating through a backpressure regulator.

18. A method to suppress bubbles in a liquid sample, contained in a measurement cell, comprising the steps, performed in sequential order, of
   1. filling said measurement cell and interconnecting fluid bearing tubing with said liquid sample by allowing said liquid sample to pass through
      a. an inlet valve,
      b. said measurement cell,
      c. an outlet from cell port; and
      d. an outlet valve;
   2. sealing said measurement cell against flow into or out of said measurement cell by closing said inlet valve and said outlet valve
   3. opening a pressurization valve;
   4. applying pressure through said pressurization valve, and subsequently through a flow impedance means comprising a narrow bore capillary tubing, to said liquid sample contained in said measurement cell such that measured interference from any bubbles present in said liquid sample is reduced, wherein said flow impedance means limits the rate at which said measurement cell is pressurized, thereby mitigating mechanical stress thereto; and
   5. measuring properties of said liquid sample in said pressurized measurement cell.

19. The method of claim 18 where said pressure is applied by means of a compressed gas cylinder.

20. The method of claim 18 where said pressure is applied by means of a piston.

21. The method of claim 18 where said pressure is applied by means of a liquid pump.

22. The method of claim 18 where said measurement cell is filled by means of a manually operated syringe.

23. The method of claim 18 where said measurement cell is filled by means of an autosampler.

24. The method of claim 18 where said measurement cell is filled by means of a syringe pump.

25. The method of claim 18 comprising the further steps, performed in sequential order, after said measurement of said properties of said liquid sample, of
   A. closing said pressurization valve;
   B. opening said outlet valve, permitting, thereby, flow to waste; and
   C. opening said inlet valve such that a subsequent liquid sample may be introduced into said measurement cell.

* * * * *